United States Patent [19]

Ilvespää

[11] 4,058,617
[45] Nov. 15, 1977

[54] IMIDAZOLES AND PHARMACEUTICAL COMPOSITION

[75] Inventor: Atso Ilvespää, Neuallschwil, Switzerland

[73] Assignee: Ciba-Geigy Corporation, Ardsley, N.Y.

[21] Appl. No.: 710,993

[22] Filed: Aug. 2, 1976

Related U.S. Application Data

[62] Division of Ser. No. 402,668, Oct. 2, 1973, Pat. No. 3,998,952.

[30] Foreign Application Priority Data

Oct. 4, 1972 Switzerland .................. 14481/72

[51] Int. Cl.² ................ C07D 403/14; C07D 277/38; A61K 31/38
[52] U.S. Cl. ................ 424/270; 260/250 AH; 260/250 BN; 260/256.4 C; 260/256.4 R; 260/256.4 N; 260/268 H; 260/293.7; 260/302 H; 260/306.7 T; 260/306.8 D; 544/60; 544/139; 544/194; 544/212; 548/313; 548/309
[58] Field of Search .............. 260/306.8 D; 424/270

[56] References Cited

U.S. PATENT DOCUMENTS

| | | | |
|---|---|---|---|
| 3,452,035 | 6/1969 | Berkelhammer et al. | 260/306.8 D |
| 3,798,232 | 5/1974 | Wittekind et al. | 260/306.8 D |

Primary Examiner—Donald G. Daus
Assistant Examiner—James H. Turnipseed
Attorney, Agent, or Firm—John J. Maitner

[57] ABSTRACT

Imidazoles of the formula I

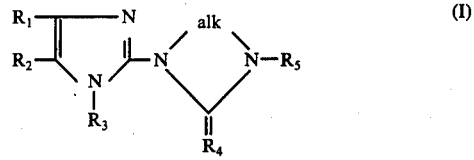

wherein one of the radicals $R_1$ and $R_2$ denotes hydrogen or lower alkyl and the other denotes the nitro group, $R_3$ is lower alkyl, hydroxy-lower alkyl, lower alkoxy-lower alkyl, lower alkylsulphonyl-lower alkyl or amino-lower alkyl, $R_4$ is oxo or thioxo, $R_5$ — if $R_1$ is the nitro group — is hydrogen, lower alkyl, hydroxy-lower alkyl, lower alkoxy-lower alkyl, amino-lower alkyl, acyl, aryl or a heterocyclic radical or $R_5$ — if $R_2$ is the nitro group — is aryl or a heterocyclic radical, with the exception of an optionally substituted 2-imidazolyl group, and alk is lower alkylene and their therapeutically usable salts, S-oxides, sulphones or N-oxides are useful as agents against amoebae, schistosomes, filariae, trichomonades and bacteria and as intermediates.

5 Claims, No Drawings

IMIDAZOLES AND PHARMACEUTICAL COMPOSITION

CROSS-REFERENCE TO RELATED APPLICATIONS

This is a division of application Ser. No. 402,668, filed Oct. 2, 1973 (now U.S. Pat. No. 3,998,952).

The invention relates to new imidazoles of the formula

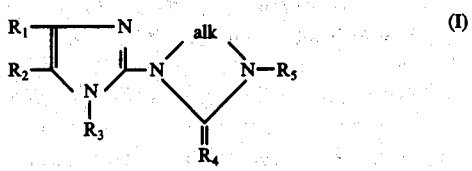

wherein one of the radicals $R_1$ and $R_2$ denotes hydrogen or lower alkyl and the other denotes the nitro group, $R_3$ is lower alkyl, hydroxy-lower alkyl, lower alkoxy-lower alkyl, lower alkyl-sulphonyl-lower alkyl or amino-lower alkyl, $R_4$ is oxo or thioxo, $R_5$ — if $R_1$ is the nitro group — is hydrogen, lower alkyl, hydroxy-lower alkyl, lower alkoxy-lower alkyl, amino-lower alkyl, acyl, aryl or a heterocyclic radical or $R_5$ — if $R_2$ is the nitro group — is aryl or a heterocyclic radical, with the exception of an optionally substituted 2-imidazolyl group, and alk is lower alkylene, as well as processes for their manufacture.

In the preceding and following text, lower radicals are above all radicals which contain up to 7 C atoms, especially up to 4 C atoms.

Examples of lower alkyl radicals are methyl, ethyl, n-propyl or isopropyl or straight-chain or branched butyl, pentyl, hexyl or heptyl, which can be bonded in any desired position.

Hydroxy-lower alkyl groups are above all those with at most 7 C atoms, preferably with at most 4 C atoms, in which the lower alkyl part has the above meaning, such as, for example, hydroxymethyl, 3-hydroxy-n-propyl and especially 2-hydroxyethyl.

Examples of lower alkoxy-lower alkyl radicals are those which possess up to 7 C atoms, preferably up to 4 C atoms, in each of the lower alkyl parts, for example methoxy-methyl, ethoxymethyl, n-propoxymethyl, n-butoxymethyl, 2-(n-butoxy)-ethyl, 3-(n-propoxy)-propyl or especially 2-methoxy-ethyl.

Lower alkylsulphonyl-lower alkyl is, for example, a lower alkyl mentioned above which carries a lower alkyl-sulphonyl group, with the lower alkyl part having the above meanings, such as methylsulphonylmethyl, ethylsulphonylmethyl, 2-methylsulphonylethyl, n-propylsulphonylmethyl, 2-n-propyl-sulphonylethyl, 3-n-propylsulphonyl-n-propyl or ethylsulphonyl-ethyl, especially 2-ethylsulphonylethyl.

Amino-lower alkyl is, for example, a lower alkyl mentioned above which carries an amino group, especially a tertiary amino group. A tertiary amino group is, for example, di-lower alkylamino, such as dimethyl-amino, N-methyl-N-ethylamino, diethylamino, di-n-propylamino or di-n-butyl-amino, or lower alkyleneamino wherein the lower alkylene part can also be interrupted by hetero-atoms, such as oxa-lower alkyleneamino, thia -lower alkyleneamino or aza-lower alkyleneamino, for example pyrrolidino, piperidino, morpholino, thiomorpholino, 2,6-dimethyl-thiomorpholino, piperazino, N'-methylpiperazino or N'-(β-hydroxy-ethyl)-piperazino. Accordingly, amino-lower alkyl is, for example, dimethylaminomethyl, diethylaminomethyl, 2-dimethylaminomethyl, pyrrolidinomethyl, 2-pyrrolidino-ethyl, 3-pyrrolidino-n-propyl, piperidino-methyl, morpholino-methyl, 2-morpholino-ethyl, 2-thiomorpholino-ethyl, piperazino-methyl, 2-piperazino-ethyl, N'-methyl-piperazino-methyl, 3-(N'-methylpiperazino)-n-propyl and N'-(β-hydroxyethyl)-piperazino-methyl.

Acyl is, for example, alkanoyl, especially lower alkanoyl, such as propionyl, butyryl or especially acetyl or formyl, and also optionally substituted benzoyl, for example benzoyl substituted as indicated below for the aryl radicals.

Aryl $R_5$ is an optionally substituted aryl radical, for example a monosubstituted, disubstituted or polysubstituted phenyl or naphthyl radical or an unsubstituted phenyl or naphthyl radical and also, for example, an optionally substituted 5,6,7,8-tetrahydro-1-or -2-naphthyl radical. An optionally monosubstituted or disubstituted phenyl or naphthyl radical is preferred, an optionally monosubstituted phenyl radical or naphthyl radical being preferred in particular, and an optionally monosubstituted phenyl radical being preferred very particularly.

An aryl radical $R_5$ is, for example, substituted by the lower alkyl groups defined above.

An aryl radical $R_5$ can, however, also be substituted by a lower alkoxy group defined above.

The aryl radical $R_5$ can also be substituted by halogen atoms or by the trifluoromethyl group.

Possible halogen atoms are in particular chlorine atoms or bromine atoms, but especially fluorine.

A hetercyclic radical is, in particular, a heterocyclic radical of aromatic or aliphatic character. Heterocyclic radicals are bonded via an atom which is a member of a heterocyclic ring.

A heterocyclic radical $R_5$ of aromatic character is, for example, a mononuclear or polynuclear radical of aromatic character which contains at least one heterocyclic ring of aromatic character, possessing at least one hetero-atom, as a constituent. Examples of suitable hetero-atoms are oxygen, sulphur and/or nitrogen atoms.

Suitable radicals of this nature are, for example, radicals possessing at least one five-membered ring which contain at least one hetero-atom, especially one of those mentioned above, such as furyl, benzo[b]furyl, thienyl, benzo[b]thienyl, pyrrolyl, indolyl, oxazolyl, thiazolyl, isooxazolyl, isothiazolyl, pyrazolyl, 3H-pyrazolyl, indazolyl, imidazolyl, furazanyl and triazolyl, such as, for example, 1H-or 2H-1,2,4-triazolyl, radicals, thiadiazolyl radicals and tetrazolyl radicals, as well as radicals possessing at least one six-membered ring which contain at least one hetero-atom, especially one of those mentioned above, such as pyridyl, quinolyl, isoquinolyl, acridinyl, pyrazinyl, pyrimidinyl, pyridazinyl, quinoxalinyl, phenazinyl, 1,3,5-triazinyl and 1,2,4-triazinyl radicals.

The heterocyclic radicals of aromatic character can be monosubstituted, disubstituted or polysubstituted, but are preferably unsubstituted.

Possible substituents on carbon atoms of the heterocyclic radicals of aromatic character which have been mentioned are in particular lower alkoxy groups, such as methoxy, ethoxy, propoxy and butoxy groups, trifluoromethyl groups, optionally substituted amino groups, nitro groups, and especially hydroxyl groups, halogen atoms, such as fluorine, chlorine and bromine atoms, and above all lower alkyl radicals, such as methyl, ethyl, propyl and isopropyl radicals, straight and branched butyl, pentyl and hexyl radicals bonded in any desired position, and phenyl radicals which are optionally substituted by lower alkyl, lower alkoxy, halogen or trifluoromethyl groups, and mercapto groups.

Optionally substituted amino groups are, for example, mono- and di-lower alkylamino groups, as well as acylamino groups and N-acyl-N-lower alkylamino groups, such as methylamino, ethylamino, dimethylamino, diethylamino, lower alkanoylamino, for example acetylamino, N-lower alkanoyl-N-lower alkylamino, for example N-acetyl-N-methylamino, benzoylamino and N-benzoyl-N-methylamino groups.

In heterocyclic radicals which carry a hydrogen atom on a ring nitrogen atom, the hydrogen atom can also be replaced by lower alkyl radicals or acyl radicals, especially benzoyl radicals which are optionally substituted, for example as indicated below for the aryl radicals, and above all lower alkanoyl radicals, for example propionyl, butyryl and especially acetyl radicals.

In heterocyclic radicals, oxidisable hetero-atoms can also be present in the form of their oxides. Thus it is in particular possible for sulphur atoms to be S-oxidised or S-dioxidised and, above all, for nitrogen atoms to be N-oxidised.

The free valency of the heterocyclic radicals of aromatic character in particular starts from a C atom belonging to the aromatic system.

A heterocyclic radical $R_5$ of aliphatic character is, for example, a monocyclic or polycyclic radical of aliphatic character which contains, as a constituent, at least one heterocyclic ring of aliphatic character possessing at least one hetero-atom, such as one of those mentioned above.

Suitable radicals of this nature are, for example, radicals possessing at least one five-membered ring which contain at least one hetero-atom, especially one of those mentioned above, such as tetrahydrofuryl, tetrahydrothienyl, pyrrolidinyl, indolinyl, pyrazolinyl, pyrazolidinyl, 4,5-alkylenethiazolyl-(2), 4,5-dihydro-thiazolyl, tetrahydro-thiazolyl, imidazolinyl and imidazolidinyl radicals, as well as radicals possessing at least one six-membered ring which contain at least one hetero-atom, especially one of those mentioned above, such as pyranyl, for example 2H- and 4H-pyranyl, tetrahydropyranyl, thiopyranyl, for example 2H- and 4H-thiopyranyl, tetrahydrothiopyranyl, tetrahydropyridyl, for example 1,2,3,4-tetrahydropyridyl, piperidyl, 1,2,3,4-tetrahydroquinolyl, oxazinyl, such as 2H-1,2-, 4H-1,2-, 6H-1,2-, 2H-1,3-, 4H-1,3-, and 4H-1,4-oxazinyl, morpholinyl, thiazinyl, for example 2H-1,3-thiazinyl, thiomorpholinyl and piperazinyl radicals.

The heterocyclic radicals of aliphatic character can be monosubstituted, disubstituted or polysubstituted, but are preferably unsubstituted.

Possible substituents at carbon atoms of the heterocyclic radicals of aliphatic character which have been mentioned are in particular alkoxy radicals, halogen atoms, hydroxyl groups and optionally substituted amino groups, such as those mentioned above, and above all lower alkyl radicals, such as those mentioned above.

Ring nitrogen atoms carrying hydrogen atoms can be substituted, in particular as indicated above, and oxidisable hetero-atoms can be in the form of their oxides, especially as indicated above.

The free valency of the heterocyclic radicals of aliphatic character in particular starts from a C atom belonging to the heterocyclic structure.

Lower alkylene is branched or, in particular, straight-chain lower alkylene, for example with 2–4 C atoms in the alkylene chain, such as 1,2-propylene, 1,2-butylene, 1,2-pentylene, 1,2-hexylene, 2-methyl-1,2-propylene, 2,3-butylene, 1,3-butylene, 1,3-propylene, 1,4-butylene or especially 1,2-ethylene.

The new compounds possess valuable pharmacological properties. In particular, they display effects against bacteria, especially Gram-negative germs, protozoa and worms, such as trichomonodes, schistosomes, coccidiae, filariae and above all amoebae, as can be shown in animal experiments, for example on the liver of healthy hamsters which is artificially infected with Entamoeba histolytica, on oral administration of about 30 to about 100 mg/kg. The new imidazoles therefore in particular are useful as agents against amoebae, schistosomes, filariae, trichomonades and bacteria. Furthermore, the new imidazoles can serve as starting products or intermediate products for the manufacture of other compounds, especially therapeutically active compounds.

Compounds preferred in particular are those of the formula Ia

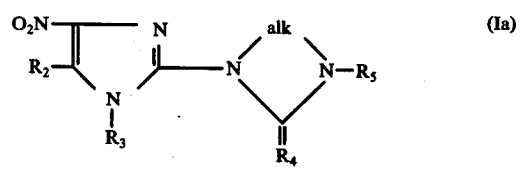

wherein $R_2$ is hydrogen or lower alkyl, $R_3$ is lower alkyl, hydroxy-lower alkyl, lower alkoxy-lower alkyl, lower alkylsulphonyl-lower alkyl or amino-lower alkyl, $R_4$ is oxo or thioxo and $R_5$ is hydrogen, lower alkyl, hydroxy-lower alkyl, lower alkoxy-lower alkyl, amino-lower alkyl, an alkanoyl group, an optionally monosubstituted, disubstituted or polysubstituted phenyl or naphthyl radical, an optionally substituted furyl, benzo[b]furyl, thienyl, benzo[b]thienyl, pyrrolyl, indolyl, oxazolyl, thiazolyl, isoxazolyl, isothiazolyl, pyrazolyl, 3H-pyrazolyl, indazolyl, imidazolyl-(4), imidazolyl-(5), imidazolyl-(2), furazanyl, triazolyl, thiadiazolyl, pyridyl, quinolyl, isoquinolyl, acridinyl, pyrazinyl, pyrimidinyl, pyridazinyl, quinoxalinyl, phenazinyl, 1,3,5- or 1,2,4-triazinyl, tetrahydrofuryl, tetrahydrothienyl, pyrrolidinyl, indolinyl, pyrazolinyl, pyrazolidinyl, 4,5-dihydro-thiazolyl, tetrahydro-thiazolyl, imidazolinyl, imidazolidinyl, pyranyl, tetrahydropyranyl, thiopyranyl, tetrahydrothiopyranyl, tetrahydropyridyl, piperidyl, 1,2,3,4-tetrahydroquinolyl, oxazinyl, morpholinyl, thiazinyl, thiomorpholinyl or piperazinyl radical or an optionally C-lower alkylated pyrrolidino, piperidino, morpholino, thiomorpholino, piperazino, N'-lower alkyl-piperazino, R'-β-hydroxyethyl-piperazino or pyridinium radical and alk is lower alkylene, and their S-oxides, sulphones or N-oxides.

Imidazoles to be singled out much more are those of the formula Ib

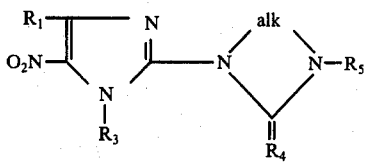

wherein $R_1$ is hydrogen or lower alkyl, $R_3$ is lower alkyl, hydroxy-lower alkyl, lower alkoxy-lower alkyl, lower alkyl-sulphonyl-lower alkyl or amino-lower alkyl, $R_4$ is oxo or thioxo and $R_5$ is an optionally monosubstituted, disubstituted or polysubstituted phenyl or naphthyl radical, an optionally substituted furyl, benzo[b]furyl, thienyl, benzo[b]thienyl, pyrrolyl, indolyl, oxazolyl, thiazolyl, isoxazolyl, isothiazolyl, pyrazolyl, 3H-pyrazolyl, indazolyl, imidazolyl-(4), imidazolyl-(5), furazanyl, triazolyl, thiadiazolyl, pyridyl, quinolyl, isoquinolyl, acridinyl, pyrazinyl, pyrimidinyl, pyridazinyl, quinoxalinyl, phenazinyl, 1,3,5-or 1,2,4-triazinyl, tetrahydrofuryl, tetrahydrothienyl, pyrrolidinyl, indolinyl, pyrazolinyl, pyrazolidinyl, 4,5-dihydro-thiazolyl, tetrahydro-thiazolyl, imidazolinyl, imidazolidinyl, pyranyl, tetrahydropyranyl, thiopyranyl, tetrahydro-thiopyranyl, tetrahydropyridyl, piperidyl, 1,2,3,4-tetrahydroquinolyl, oxazinyl, morpholinyl, thiazinyl, thiomorpholinyl or piperazinyl radical, or an optionally C-lower alkylated pyrrolidino, piperidino, morpholino, thiomorpholino, piperazino, N'-lower alkyl-piperazino, N'-β-hydroxyethyl-piperazino or pyridinium radical and alk is lower alkylene, and their S-oxides, sulphones or N-oxides.

Compounds to be singled out particularly are compounds Ic of the formula Ia, wherein $R_2$ is hydrogen or lower alkyl, $R_3$ is lower alkyl, hydroxy-lower alkyl, lower alkoxy-lower alkyl, lower alkylsulphonyl-lower alkyl, di-lower alkylamino-lower alkyl, lower alkyleneamino-lower alkyl, lower oxaalkyleneamino-lower alkyl, or lower thiaalkyleneamino-lower alkyl, $R_4$ is oxo or thioxo and $R_5$ is hydrogen, lower alkyl, hydroxy-lower alkyl, lower alkoxy-lower alkyl, di-lower alkylamino-lower alkyl, lower alkyleneamino-lower alkyl, lower oxaalkyleneamino-loweralkyl, lower thiaalkyleneamino-lower alkyl, lower azaalkyleneamino-lower alkyl, lower alkanoyl, an optionally monosubstituted, disubstituted or polysubstituted phenyl radical, an optionally substituted furyl, thienyl, pyrrolyl, indolyl, oxazolyl, thiazolyl, thiadiazolyl, 4,5-dihydro-thizolyl-(2), tetrahydro-thiazolyl-(2), pyrazolyl, indazolyl, imidazolyl-(5), imadazolyl-(4), imidazolyl-(2), pyridyl, pyrazinyl, pyrimidinyl, pyridazinyl, 1,3,5- or 1,2,4-triazinyl, pyrrolidinyl, pyrazolinyl, indolinyl, pyrazolidinyl, imidazolinyl, imidazolidinyl, piperidyl, morpholinyl, thiazinyl, thiomorpholinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and alk is 1,2-ethylene, as well as their S-oxides, sulphones or N-oxides.

Further compounds to be singled out are imidazoles Id of the formula Ib, wherein $R_1$ is hydrogen or lower alkyl, $R_3$ is lower alkyl, hyroxy-lower alkyl, lower alkoxy-lower alkyl, lower alkylsulphonyl-lower alkyl, di-lower alkylamino-lower alkyl, lower alkyleneamino-lower alkyl, lower oxaalkyleneamino-lower alkyl, lower thiaalkyleneamino-lower alkyl, or lower azaalkyleneamino-lower alkyl, $R_4$ is oxo or thioxo, and $R_5$ is an optionally monosubstituted, disubstituted or polysubstituted phenyl radical, an optionally substituted furyl, thienyl, pyrrolyl, indolyl, oxazolyl, thiazolyl, thiadiazolyl, 4,5-dihydro-thiazolyl-(2), tetrahydro-thiazolyl-(2), pyrazolyl, indazolyl, imidazolyl-(5), imidazolyl-(4), pyridyl, pyrazinyl, pyrimidinyl, pyridazinyl, 1,3,5- or 1,2,4-triazinyl, pyrrolidinyl, pyrazolinyl, indolinyl, pyrazolidinyl, imidazolinyl, imidazolidinyl, piperidyl, morpholinyl, thiazinyl, thiomorpholinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and alk is 1,2-ethylene, as well as their S-oxides, sulphones or N-oxides.

Further compounds to be singled out are compounds Ie of the formula Ia, wherein $R_2$ is hydrogen or lower alkyl, $R_3$ is hydroxy-lower alkyl or lower alkyl, $R_4$ is oxo or thioxo and $R_5$ is hydrogen, lower alkyl, hydroxy-lower alkyl, lower alkoxy-lower alkyl, lower alkanoyl, an optionally monosubstituted phenyl radical or an optionally substituted thiazolyl, imidazolyl-(5), 4,5-dihydro-thiazolyl-(2), tetrahydro-thiazolyl-(2), imidazolyl-(4), imidazolyl-(2), pyridyl, thiadiazolyl, morpholinyl, thiomorpholinyl, pyrimidinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and alk is 1,2-ethylene, as well as their S-oxides, sulphones or N-oxides.

Compounds also to be singled out are compounds If of the formula Ib, wherein $R_1$ is hydrogen or lower alkyl, $R_3$ is hydroxy-lower alkyl or lower alkyl, $R_4$ is oxo or thioxo and $R_5$ is an optionally monosubstituted phenyl radical or an optionally substituted thiazolyl, imidazolyl-(5), 4,5-dihydro-thiazolyl-(2), tetrahydro-thiazolyl-(2), imidazolyl-(4), pyridyl, thiadiazolyl, morpholinyl, thiomorpholinyl, pyrimidinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and alk is ethylene, as well as their S-oxides, sulphones or N-oxides.

Compounds to be particularly singled out are compounds Ig of the formula Ia, wherein $R_2$ is hydrogen or lower alkyl, $R_3$ is hydroxy-lower alkyl or lower alkyl, $R_4$ is oxo or thioxo and $R_5$ is hydrogen, lower alkyl, hydroxy-lower alkyl, lower alkoxy-lower alkyl, lower alkanoyl, an optionally o-, m- or p-halogenated phenyl radical or an optionally substituted thiazolyl, 4,5-dihydro-thiazolyl-(2), tetrahydro-thiazolyl-(2), imidazolyl-(5), imidazolyl-(4), imidazolyl-(2), thiadiazolyl, pyridyl, or morpholinyl radical, an optionally lower alkylated thiomorpholinyl radical, optionally lower alkylated pyrimidinyl radical or optionally lower alkylated piperazinyl radical, an optionally C-lower alkylated pyrrolidino, piperidino, morpholino, thiomorpholino, N-piperazino, N'-lower alkylpiperazino, N'-β-hydroxyethyl-piperazino or pyridinium radical and alk is ethylene, as well as their S-oxides, sulphones or N-oxides.

Compounds which are equally suitable are compounds Ih of the formula Ib, wherein $R_1$ is hydrogen or lower alkyl, $R_3$ is hydroxy-lower alkyl or lower alkyl, $R_4$ is oxo or thioxo and $R_5$ is an optionally o-, m- or p-halogenated phenyl radical, or an optionally substituted thiazolyl, 4,5-dihydro-thiazolyl-(2), tetrahydro-thiazolyl-(2), imidazolyl-(5), imidazolyl-(4), thiadiazolyl, pyridyl, morpholinyl, optionally lower alkylated thiomorpholinyl, optionally lower alkylated pyrimidinyl or optionally lower alkylated piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and alk is ethylene, as well as their S-oxides, sulphones or N-oxides.

Suitable compounds are above all those of the formula Ia wherein $R_2$ is hydrogen or lower alkyl, $R_3$ is hydroxy-lower alkyl or lower alkyl, $R_4$ is oxo or thioxo and $R_5$ is hydrogen, lower alkyl, hydroxy-lower alkyl, lower alkoxy-lower alkyl, propionyl, butyryl, acetyl, formyl, phenyl, o-, m- or p-fluorophenyl, 4-thiazolyl, 2-thiazolyl, 4,5-dimethyl-thiazolyl-(2), cyclopentano-[1,2-d]-thiazolyl-(2), 5-amino-1,3,4-thiadiazolyl-(2), 4,5-dihydro-thiazolyl-(2), tetrahydro-thiazolyl-(2), 4-acetyl-thiazolyl-(2), 5-acetyl-thiazolyl-(2), 5-methylsulphonyl-thiazolyl-(2), pyridyl-(2), pyridyl-(3), pyridyl-(4), 4,6-dimethyl-pyridyl-(2), 3,5-dimethyl-pyridyl-(2), pyrimidinyl-(2), pyrimidinyl-(5), 2,6-dihydroxy-pyrimidinyl-(4), 2,4-dimethyl-pyrimidinyl-(5), 4,6-dimethyl-pyrimidinyl-(2), pyrrolidinyl-(2), piperidyl-(3), imidazolyl-(2), imidazolyl-(4), imidazolyl-(5), thiadiazolyl-(2), 5-methyl-thiadiazolyl-(2), 5-ethyl-thiadiazolyl-(2), or an optionally C-lower alkylated pyridinium radical and alk is ethylene.

Compounds which are very much more suitable are those of the formula Ib wherein $R_1$ is hydrogen or lower alkyl, $R_3$ is hydroxy-lower alkyl or lower alkyl, $R_4$ is oxo or thioxo and $R_5$ is phenyl, o-, m- or p-fluorophenyl, 4-thiazolyl, 2-thiazolyl, 4,5-dimethyl-thiazolyl-(2), cyclopentano-[1,2-d]-thiazolyl-(2), 5-amino-1,3,4-thiadiazolyl-(2), 4,5-dihydro-thiazolyl-(2), tetrahydro-thiazolyl-(2), 4-acetyl-thiazolyl-(2), 5-acetyl-thiazolyl-(2), 5-methylsulphonyl-thiazolyl-(2), pyridyl-(2), pyridyl-(3), pyridyl-(4), 4,6-dimethyl-pyridyl-(2), 3,5-dimethyl-pyridyl-(2), pyrimidinyl-(2), pyrimidinyl-(5), 2,6-dihydroxy-pyrimidinyl-(4), 2,4-dimethyl-pyrimidinyl-(5), 4,6-dimethyl-pyrimidinyl-(2), pyrrolidinyl-(2), piperidyl-(3), piperidyl-(1), imidazolyl-(4), imidazolyl-(5), thiadiazolyl-(2), 5-methyl-thiadiazolyl-(2), 5-ethyl-thiadiazolyl-(2) or an optionally C-lower alkylated pyridinium radical and alk is ethylene.

Particularly suitable compounds are those of the formula Ia, wherein $R_2$ is hydrogen or methyl, $R_3$ is 2-hydroxyethyl or methyl, $R_4$ is oxo, $R_5$ is hydrogen, methyl, hydroxymethyl, propionyl, acetyl, formyl, phenyl, p-fluorophenyl, thiazolyl-(2), cyclopentano-[1,2-d]-thiazolyl-(2), 5-acetyl-thiazolyl-(2), 5-methylsulphonyl-thiazolyl-(2), pyridyl-(2), pyrimidinyl-(2), thiadiazolyl-(2) or 5-ethyl-thiadiazolyl-(2) and alk is ethylene.

Even more suitable compounds are those of the formula Ib wherein $R_1$ is hydrogen or methyl, $R_3$ is 2-hydroxyethyl or methyl, $R_4$ is oxo, $R_5$ is phenyl, p-fluorophenyl, thiazolyl-(2), cyclopentano[1,2-d]-thiazolyl-(2), 5-acetyl-thiazolyl-(2), 5-methylsulphonyl-thiazolyl-(2), pyridyl-(2), pyrimidinyl-(2), piperidyl-(3), thiadiazolyl-(2) or 5-ethyl-thiadiazolyl-(2) and alk is ethylene.

Amongst these new imidazoles of the formula I there should in particular be mentioned 1,3-di-[1-methyl-5-nitro-imidazolyl-(2)]-2-oxo-tetrahydroimidazole, 1-[thiazolyl-(2)]-2-oxo-3-[1-methyl-4-nitro-imidazolyl-(2)]-tetrahydroimidazole, 1-[5-methylsulphonyl-thiazolyl-(2)]-2-oxo-3-[1-methyl-5-nitro-imidazolyl-(2)]-tetrahydroimidazole, 1-[pyrimidinyl-(2)]-2-oxo-3-[1-methyl-5-nitro-imidazolyl-(2)]-tetrahydroimidazole, 1-[1,3,4-thiadiazolyl-(2)]-2-oxo-3-[1-methyl-5-nitro-imidazolyl-(2)]-tetrahydroimidazole, 1-[cyclopentano-[1,2-d]-thiazolyl-(2)]-2-oxo-3-[1-methyl-5-nitro-imidazolyl-(2)]-tetrahydroimidazole and especially 1-[thiazolyl-(2)]-2-oxo-3-[1-methyl-5-nitroimidazolyl-(2)]-tetrahydroimidazole.

The new imidazoles are obtained according to methods which are in themselves known.

Thus, for example, the new imidazoles can be manufactured by reacting an imidazole of the formula II

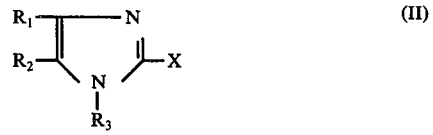

wherein $R_1$, $R_2$ and $R_3$ have the above meaning and X is a reactive esterified hydroxyl group, a reactive etherified hydroxyl group, a free or etherified mercapto group, an ammonium group or especially a sulphonyl group, with a compound of the formula III

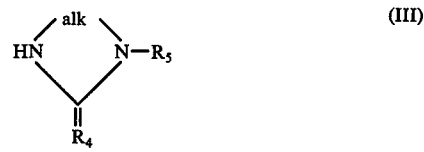

wherein $R_4$, $R_5$ and alk have the above meaning.

A reactive esterified hydroxyl group X is, in particular, a hydroxyl group esterified by a strong inorganic or organic acid, above all a hydrogen halide acid, such as hydrochloric acid, hydrobromic acid or hydriodic acid, also sulphuric acid or an organic sulphonic acid, such as an aromatic sulphonic acid, for example benzenesulphonic acid, p-bromobenzenesulphonic acid or p-toluenesulphonic acid, or an aliphatic sulphonic acid, such as an alkanesulphonic acid, for example methanesulphonic acid or ethanesulphonic acid. Thus, X in particular represents chlorine, bromine or iodine.

A reactive etherified hydroxyl group is, for example, a hydroxyl group etherified with an aromatic or aliphatic alcohol, above all a lower aliphatic alcohol, such as an optionally substituted phenoxy group or an alkoxy group, above all of lower alkoxy group, and especially methoxy or ethoxy.

An etherified mercapto group is, for example, an optionally substituted phenylmercapto or benzylmercapto group or, in particular, a lower alkylmercapto group, such as the ethylmercapto or methylmercapto group.

An ammonium group is, in particular, a quaternary ammonium group, above all a tri-lower alkylammonium group, for example the trimethylammonium group or triethylammonium group, or the cation of an aromatic nitrogen base, for example the pyridinium or quinolinium group.

A sulphonyl group is, in particular, a sulphonyl group derived from an organic sulphonic acid, especially from an aromatic sulphonic acid. Thus, X in particular represents benzenesulphonyl, p-bromobenzenesulphonyl, p-toluenesulphonyl or methylsulphonyl.

This reaction can be carried out in the usual manner. It is preferably carried out in the presence of a basic condensation agent, or alternatively the compound of the formula III is employed in the form of its N-metal derivative, such as its N-alkali metal derivative, which is obtainable, for example, from the compound of the formula III and an amide, hydride, hydrocarbon compound, hydroxide or alcoholate of an alkali metal, such as lithium, sodium or potassium, and which can be used without isolation. Suitable basic condensation agents are, for example, alkali metal hydroxides or alkaline earth metal hydroxides, such as sodium hydroxide, potassium hydroxide and calcium hydroxide, or organic tertiary nitrogen bases, such as trialkylamines, for example trimethylamine and triethylamine, or pyridine. It is furthermore also possible to employ an excess of the compound of the formula III, especially if $R_5$ in a compound of the formula III is not hydrogen. The reaction is advantageously carried out at elevated temperature and/or in the presence of an inert solvent, such as solvent possessing polar functional groups, for example dimethylformamide, dimethylacetamide, dimethylsulphoxide, acetonitrile or cyclic aliphatic ethers, such as dioxane and tetrahydrofurane.

In resulting compounds, substituents can be introduced, modified or split off within the scope of the definition of the end products.

Thus it is possible, in resulting compounds in which $R_3$ is hydroxy-lower alkyl, to convert $R_3$ in the usual manner into a lower alkoxy-lower alkyl radical. Thus it is possible, for example, to react a resulting hydroxy-lower alkyl compound with a reactive ester, for example one of those mentioned above, of a lower alkanol, preferably in the presence of a basic condensation agent, such as one of those mentioned, for example an alkali metal hydroxide, or with a diazo-lower alkane, such as diazomethane, preferably in the presence of boron trifluoride.

In resulting compounds in which $R_4$ is thioxo, $R_4$ can be converted into the oxo group in the usual manner, especially according to methods of hydrolysis which are in themselves known, for example by treating the resulting thioxo compounds with an alkaline agent, such as an alkali metal hydroxide, in the presence of an oxidising agent, such as hydrogen peroxide.

In resulting compounds in which $R_5$ is hydrogen, a radical $R_5$ which differs from hydrogen can be introduced in the usual manner. The introduction can in particular be achieved by reacting the resulting compounds of the formula I with a compound $R_5X$, wherein $R_5$ has the above meaning but differs from hydrogen and X is a reactively esterified hydroxyl group, such as one of those mentioned, especially a halogen atom, for example a chlorine atom, or a benzenesulphonyl group. Di-lower alkyl sulphate, such as dimethylsulphate, is in particular also suitable for the alkylation reaction. If a 1-hydroxy-lower alkyl radical, for example the hydroxymethyl radical, $R_5$ is to be introduced, the resulting compound of the formula I can also be reacted with an oxo-lower alkyl, for example with formaldehyde in order to introduce hydroxymethyl. If a 2-hydroxy-lower alkyl radical, for example the 2-hydroxyethyl radical, $R_5$ is to be introduced, the resulting compound can also be reacted with a 1,2-epoxy-lower alkyl, for example with ethylene oxide in order to introduce 2-hydroxyethyl. The reaction is preferably carried out in a neutral or weakly acid medium.

Thus it is possible, for example, to react resulting compounds of the formula VII

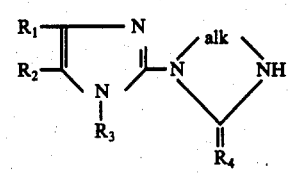

(VII)

wherein $R_1$, $R_2$, $R_3$, $R_4$ and alk have the above meaning, with a compound of the formula X-$R_5$, wherein $R_5$ has the above meaning and X is a reactive esterified hydroxyl group, a reactive etherified hydroxyl group, a free or etherified mercapto group, an ammonium group or a sulphonyl group.

A reactive esterified hydroxyl group, a reactive etherified hydroxyl group, a free or etherified mercapto group, an ammonium group and a sulphonyl group are groups such as have been described above.

The reaction can be carried out in the usual manner. It is preferably carried out under the same conditions as have been described for the reaction of compounds of the formula II with compounds of the formula III.

Resulting compounds in which $R_5$ is hydrogen can be acylated in the usual manner, especially by reaction with an acylating agent. Possible acylating agents are carboxylic acids, preferably in the form of their functional derivatives, such as halides, especially chlorides, or anhydrides, for example pure or mixed anhydrides, or internal anhydrides, such as ketenes, or esters, such as esters with lower alkanols, such as methanol or ethanol, or cyanomethyl esters.

In resulting compounds in which $R_5$ is acyl, it is possible to replace $R_5$ by hydrogen in the usual manner. Thus it is possible to hydrolyse an acylamino compound, preferably catalysed by acids, for example by hydrochloric acid or sulphuric acid.

In resulting compounds in which $R_5$ is hydroxy-lower alkyl, $R_5$ can be converted into a lower alkoxy-lower alkyl radical in the usual manner, for example as described for the conversion of $R_3$. However, it is also possible to convert a hydroxy-lower alkyl radical $R_5$ into an amino-lower alkyl radical in the usual manner. Thus it is possible first to convert a resulting hydroxy-lower alkyl compound into a compound possessing a reactively esterified hydroxy-lower alkyl radical, a reactive ester being, in particular, an ester of strong inorganic or organic acids, such as, in particular, hydrogen halide acids, for example hydrochloric acid, hydrobromic acid or hydriodic acid, toluenesulphonic acids, such as, in particular, arylsulphonic acids, for example benzenesulphonic acid or toluenesulphonic acids, alkylsulphonic acids or sulphuric acid. For example, a hydroxy-lower alkyl compound can be converted into a halogeno-lower alkyl compound by treatment with halogenating agents, such as thionyl chloride, phosphorus oxychloride or phosphorus pentabromide. In the resulting reactive ester the reactively esterified hydroxyl group can then be replaced in the usual manner by an amino group, for example by treatment with corresponding amines.

In compounds of the general formula I which possess an amino-lower alkyl group with at least one hydrogen atom bonded to a nitrogen atom as $R_3$, the hydrogen atom can be substituted in the usual manner. Thus it is in particular possible to follow the procedure of reacting a compound of the formula I, in which $R_3$ is a primary or secondary amino group, with a reactive ester of an alcohol corresponding to a substituent of the amino group of the amino-lower alkyl radical.

Furthermore it is possible to N-oxidise an imidazole of the formula I which carries a N-heterocyclic radical as the radical $R_5$.

The oxidation is carried out in the usual manner, for example with N-oxidising agents, such as hydrogen peroxide, ozone, inorganic per-acids, for example persulphuric acids, such as Caro's acid, or especially organic peroxy compounds, above all organic per-acids, such as peracetic acid, pertrifluoroacetic acid, perbenzoic acid or monoperphthalic acid, which can also be substituted, for example by halogen atoms, such as chlorine atoms, for instance chloromonoperphthalic acid or m-chloroperbenzoic acid or tertiary hydroperoxide compounds, such as tert.-butyl peroxide or cumene peroxide, optionally in the presence of catalysts such as vanadium, titanium or molybdenum compounds.

Resulting compounds of the formula I, in which $R_5$ is a N-oxidised N-heterocyclic radical, can be converted by reduction into the corresponding compounds of the formula I, in which $R_5$ is a N-heterocyclic radical.

The reduction is carried out in the usual manner, advantageously by the action of phosphorus halides.

Resulting compounds of the formula I, in which the aliphatic radical $R_5$ is a S-unsubstituted heterocyclic radical, can be oxidised to the S-oxides (sulphoxides) or S-dioxides (sulphones).

The oxidation to the sulphoxides or sulphones can be carried out in a manner which is in itself known, for example by reaction with a S-oxidising agent, such as hydrogen peroxide, per-acids, especially peracetic acid, perbenzoic acids or monoperphthalic acids, which can also be substituted, for example by halogen atoms, 1-chlorobenzotriazole, chromic acid, potassium permanganate, hypohalites or nitric acid, nitrous gases and the like, or electrolytically. In these reactions, the sulphoxides are obtained at lower temperatures, especially if good cooling is used, or if only one mol equivalent of the oxidising agent is used, whilst on warming and/or using at least 2 mol equivalents of the oxidising agent the sulphones are obtained. The oxidation to sulphoxides can in particular also be effected by reaction with 2,4,4,6-tetrabromocyclohexadienone in a solvent containing an ether, for example in dioxane/water or tetrahydrofurane, preferably in the presence of sodium acetate.

Resulting S-oxides can be oxidised to the S-dioxides. This oxidation can be effected in a manner which is in itself known, for example as in the case of the oxidation described above which leads to the dioxides.

Resulting S-oxides can be reduced to the corresponding S-unsubstituted compounds of the formula I, for example with a reducing agent, such as a di-light metal hydride, for example with sodium borohydride, or a light metal hydride such as diborane or a borohydride-etherate, for example $BH_3$-tetrahydrofurane, or above all dichloroborane or, for example, with acetyl chloride, sulphites or hydriodic acid, or especially with triphenylphosphine.

In the above reductions care must be taken, where relevant, that further groups which can be reduced are not attacked. Thus care must in particular be taken, during the reduction, that any halogen atoms bonded to aromatic rings which may be present are not replaced by hydrogen. In addition, a thioether grouping requires attention in the case of all reductions, especially catalytic hydrogenations. Very particularly, it is necessary to ensure that the nitro group ($R_1$ or $R_2$) is not reduced. Catalysts which are not affected by sulphur are preferentially to be used, and if necessary the hydrogen absorption should be followed volumetrically and the hydrogenation stopped after the calculated amount has been absorbed.

Compounds of the formula I which contain a radical $R_5$ which can be nitrated (aryl, or a heterocyclic radical of aromatic character) can be nitrated in a known manner and especially as described above.

Compounds of the formula I which contain a nitro group as the radical $R_2$ can be rearranged to give the corresponding 4-nitroimidazoles, that is to say compounds of the formula I which contain a nitro group as the radical $R_1$. Such a rearrangement is effected, for example, by the action of, for instance, an excess of alkali metal iodide, especially potassium iodide, in the presence of an inert solvent, preferably a solvent with polar functional groups, such as dimethylformamide, dimethylacetamide, dimethylsulphoxide, acetonitrile or hexamethylphosphoric acid triamide.

The rearrangement of $R_2$=nitro compounds into $R_1$=nitro compounds of the formula I can also be effected by the action of an iodide which corresponds to the radical $R_3$, namely $R_3I$, such as, for example, the action of methyl iodide on compounds of the formula I which contain a methyl group as the $R_3$ radical. In this rearrangement, the unsubstituted nitrogen atom of the imidazole ring is quaternised. Thereafter, the quaternary salt is pyrolised. This rearrangement also takes place, for example, in the presence of an inert solvent, preferably the solvents described above.

The subsequent conversions can be carried out individually or in combination and in any desired sequence. Care must be taken in the individual operations that other functional groups are not attacked.

Depending on the process conditions and the starting substances, the final substances are obtained in the free form or in the form of their acid addition salts which is also included in the invention. Thus, for example, basic, neutral or mixed salts and where relevant also hemihydrates, monohydrates, sesquihydrates or polyhydrates thereof can be obtained. The acid addition salts of the new compounds can be converted into the free compound in a manner which is in itself known, for example with basic agents, such as alkalis or ion exchangers. On the other hand, the resulting free bases can form salts with organic or inorganic acids. The acids used for the manufacture of acid addition salts are in particular those suitable for forming therapeutically usable salts. As examples of such acids there may be mentioned: hydrogen halide acids, sulphuric acids, phosphoric acids, nitric acid, perchloric acid, aliphatic, alicyclic, aromatic or heterocyclic carboxylic acids or sulphonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, or p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid and ethylenesulphonic acid; halogenobenzenesulphonic acid, toluenesulphonic acid, naphthalenesulphonic acid or sulphanilic acid; methionine, tryptophane, lysine or arginine.

These or other salts of the new compounds, such as, for example, the picrates, can also serve for the purification of the resulting free bases, by converting the free bases into salts, isolating these and again liberating the bases from the salts. Because of the close relationships between the new compounds in the free form and in the form of their salts, the free compounds are where appropriate also to be understood to include the corresponding salts, in the preceding and following text.

The invention also relates to those embodiments of the process in which a process is stopped at any stage or in which a compound obtainable as an intermediate product at any stage is used as the starting compound and the missing steps are carried out, or a starting substance is formed under the reaction conditions or used, where relevant, in the form of a salt and/or racemate or optical antipode.

Depending on the number of the asymmetrical C atoms and on the choice of the starting substances and procedures, the new compounds can be in the form of racemate mixtures, racemates or optical antipodes.

Racemate mixtures can be separated into the pure racemates on the basis of the physico-chemical differences of the constituents, in a known manner, for example by chromatography and/or fractional crystallisation.

Pure racemates can be resolved into the diastereomers according to known methods, for example by recrystallisation from an optically active solvent, with the aid of microorganisms or by reaction with an optically active acid which forms salts with the racemic compound and separation of the salts obtained in this manner, for example on the basis of their different solubilities, and from the diastereomers the antipodes can be liberated by the action of suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active of the two antipodes is isolated.

According to the invention it is, however, also possible to obtain the end products in the form of the pure racemates or optical antipodes by employing starting substances containing one or more asymmetrical C atoms in the form of the pure racemates or optical antipodes.

Appropriately, those starting substances which lead to the final substances which have initially been particularly singled out are employed for carrying out the reactions according to the invention.

The starting substances are known or can, if they are new, be obtained according to methods which are in themselves known. New starting substances also form a subject of the invention.

The reactions mentioned are carried out in the usual manner in the presence or absence of diluents, condensation agents and/or catalytic agents, at lowered, ordinary or raised temperature, optionally in a closed vessel. If appropriate, the reaction is carried out at high dilution (dilution principle).

The new compounds can be used, for example, in the form of pharmaceutical preparations in which they are present in the free form or optionally in the form of their salts, especially the therapeutically usable salts, mixed with a pharmaceutical, organic or inorganic, solid or liquid excipient which is suitable, for example, for enteral or parenteral administration. Possible substances which can form the excipient are those which do not react with the new compounds such as, for example, water, gelatine, lactose, starch, stearyl alcohol, magnesium stearate, talc, vegetable oils, benzyl alcohols, gum, propylene glycols, white petroleum jelly or other known medicinal excipients. The pharmaceutical preparations can, for example, be in the form of tablets, dragées, capsules or suppositories or in a liquid form as solutions (for example as an elixir or syrup), suspensions or emulsions. They are optionally sterilised and/or contain auxiliaries, such as preservatives, stabilisers, wetting agents or emulsifiers, solubilising agents or salts for regulating the osmotic pressure or buffers. They can also contain other therapeutically valuable substances. The pharmaceutical preparations are formulated according to customary methods. The dosage of the new compounds can vary depending on the compound and on the individual requirements of the patient. Preferably, a daily dose of about 0.25 to 1.0 g is administered to a warm-blooded organism weighing about 70 kg.

The new compounds can also be used in veterinary medicine, for example in one of the abovementioned forms or in the form of feedstuffs or of additives to animal fodder. For this, for example, the customary extenders and diluents or feedstuffs are used.

The invention is described in more detail in the examples which follow.

EXAMPLE 1

A solution of 8.5 g of 1-[thiazolyl-(2)]-2-oxo tetrahydroimidazole in 200 ml of dimethylformamide is added dropwise over the course of 1 hour to a suspension of 2.4 g of 50% strength sodium hydride in 50 ml of dimethylformamide at 20° C to 30° C, whilst stirring. Thereafter, the mixture is stirred for a further hour at 20° C to 30° C. 10.3 g of 1-methyl-2-methylsulphonyl-5-nitro-imidazole, dissolved in 75 ml of dimethylformamide, are then added and the whole is stirred for a further hour at 90° C to 100° C. Thereafter the reaction mixture is evaporated and the evaporation residue is washed with petroleum ether, triturated with approx. 50 ml of water, filtered off and first washed thoroughly with water and then with methanol. The crude product is recrystallised from 100 ml of 2-ethoxyethanol. The 1-[thiazolyl-(2)]-2-oxo-3-[1-methyl-5-nitro-imidazolyl-(2)]-tetrahydroimidazole thus obtained, of the formula

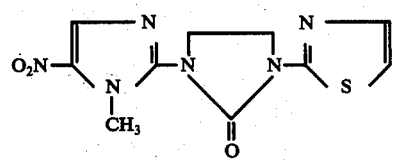

melts at 226° C.

EXAMPLE 2

10 g of 1,3-di-[1-methyl-5-nitro-imidazolyl-(2)]-2-oxo-tetrahydroimidazole (melting point 211° C–212° C), 25 g of potassium iodide and 125 ml of dimethylformamide are heated for 20 hours under reflux. The reaction mixture is then evaporated to dryness and the evaporation residue is triturated with water and filtered off. The crude product is first recrystallised from 35 ml of dimethylformamide and then again recrystallised from 50 ml of dimethylformamide. 1,3-Di-[1-methyl-4-nitro-imidazolyl-(2)]-2-oxo-tetrahydroimidazole thus obtained, of the formula

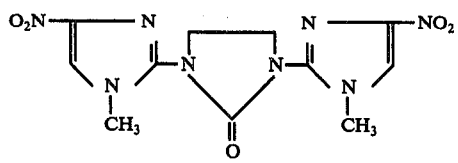

melts at 263° C–265° C.

EXAMPLE 3

A solution of 5.3 g of 1-[5-acetyl-thiazolyl-(2)]-2-oxo-tetrahydroimidazole in 100 ml of dimethylformamide is added dropwise over the course of 30 minutes to a suspension of 1.2 g of 50% strength sodium hydride in 40 ml of dimethylformamide at 20°–30° C, whilst stirring. Thereafter the mixture is stirred for a further 2 hours at 20°–30° C. 5.2 g of 1-methyl-2-methylsulphonyl-5-nitro-imidazole dissolved in 50 ml of dimethylformamide are then added and the mixture is stirred for a further hour at 90°–100° C. The reaction mixture is then evaporated and the evaporation residue is washed with petroleum ether, triturated with 100 ml of water, filtered off and first thoroughly washed with water and then with isopropanol. The resulting crude product is recrystallised from 15 ml of dimethylformamide. 1-[5-Acetyl-thiazolyl-(2)]-2-oxo-3-[1-methyl-5-nitro-imidazolyl-(2)]-tetrahydroimidazole thus obtained, of the formula

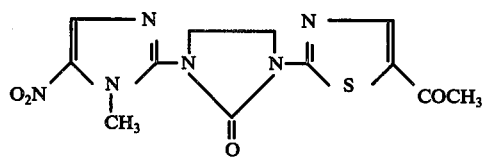

melts at 275°–277° C, with decomposition.

1-[5-Acetyl-thiazolyl-(2)]-2-oxo-tetrahydroimidazole required as the starting material, can be obtained, for example, by condensation of 2-amino-5-acetyl-thiazole with β-chloroethylisocyanate and subsequent cyclisation (for example treatment with a base, such as sodium hydroxide solution or sodium acetate). It melts at 271°–274° C, with decomposition.

EXAMPLE 4

A solution of 9.0 g of 1-(4-fluorophenyl)-2-oxo-tetrahydroimidazole in 75 ml of dimethylformamide is added dropwise over the course of 1 hour to a suspension of 2.4 g of 50% strength sodium hydride in 75 ml of dimethylformamide at 20°–30° C, whilst stirring. Thereafter the mixture is stirred for a further hour at 20°–30° C. 10.3 g of 1-methyl-2-methylsulphonyl-5-nitro-imidazole, dissolved in 75 ml of dimethylformamide, are then added and the whole is stirred for a further hour at 90°–100° C. The reaction mixture is then evaporated and the evaporation residue is triturated with 100 ml of water, filtered off and first thoroughly washed with water, then with isopropanol and finally also with petroleum ether. The crude product is recrystallised from 85 ml of 2-ethoxy-ethanol. 1-(4-Fluorophenyl)-2-oxo-3-[1-methyl-5-nitro-imidazolyl-(2)]-tetrahydroimidazole, thus obtained, of the formula

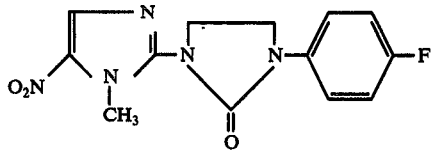

melts at 216°–218° C.

1-(4-Fluorophenyl)-2-oxo-tetrahydroimidazole required as the starting material, can be obtained, for example, by condensation of 4-fluoroaniline with β-chloroethylisocyanate and subsequent cyclisation. It melts at 148°–149° C.

EXAMPLE 5

A solution of 8.2 g of 1-[pyrimidinyl-(2)]-2-oxo-tetrahydroimidazole in 200 ml of dimethylformamide is added dropwise over the course of 40 minutes to a suspension of 2.4 g of 50% strength sodium hydride in 75 ml of dimethylformamide at 40° to 50° C. whilst stirring. Thereafter the mixture is stirred for a further 1 hour 30 minutes at 50° C. 10.3 g of 1-methyl-2-methylsulphonyl-5-nitro-imidazole dissolved in 75 ml of dimethylformamide are then added and the mixture is stirred for a further hour at 90° to 100° C. After cooling, the reaction product which has precipitated is filtered off, introduced into 70 ml of water, again filtered off and thoroughly washed with water, isopropanol and finally also with petroleum ether. 1-[Pyrimidinyl-(2)]-2-oxo-3-[1-methyl-5-nitro-imidazolyl-(2)]-tetrahydroimidazole, thus obtained, of the formula

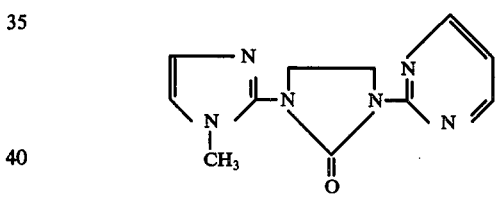

melts at 264°–266° C, with decomposition.

1-[Pyrimidinyl-(2)]-2-oxo-tetrahydroimidazole required as the starting material, can be obtained, for example, by condensation of 2-amino-pyrimidine with β-chloroethylisocyanate and subsequent cyclisation. It melts at 235°–236° C.

EXAMPLE 6

A solution of 10.5 g of 1-[cyclopentano[1,2-d]-thiazolyl-(2)]-2-oxo-tetrahydroimidazole in 200 ml of dimethylformamide is added dropwise over the course of 1 hour to a suspension of 2.4 g of 50% strength sodium hydride in 75 ml of dimethylformamide at 30° to 40° C, whilst stirring. Thereafter the mixture is stirred for a further hour at 30° to 40° C. 10.3 g of 1-methyl-2-methylsulphonyl-5-nitroimidazole dissolved in 75 ml of dimethylformamide are then added and the whole is stirred for a further hour at 90° to 100° C. The reaction mixture is then evaporated and the evaporation residue is triturated with 100 ml of water, filtered off and first thoroughly washed with water, then with isopropanol and finally also with petroleum ether. The crude product is recrystallised from 130 ml of 2-ethoxyethanol. 1-[Cyclopentano[1,2-d]-thiazolyl-(2)]-2-oxo-3-[1-methyl-5-nitroimidazolyl-(2)]-tetrahydroimidazole, thus obtained, of the formula

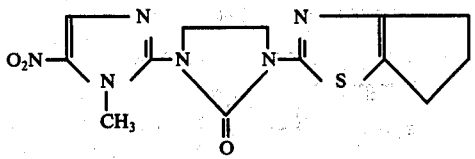

melts at 221°–222° C. 1-[Cyclopentano[1,2-d]-thiazolyl-(2)]-2-oxo-tetrahydroimidazole, required as the starting material, can be obtained, for example, by condensation of 2-amino-cyclopentano [1,2-d]-thiazole with β-chloroethylisocyanate and subsequent cyclisation. It melts at 257° C.

EXAMPLE 7

A solution of 8.2 g of 1-[pyridyl-(2)]-2-oxo-tetrahydroimidazole in 100 ml of dimethylformamide is added dropwise over the course of 1 hour to a suspension of 2.4 g of 50% strength sodium hydride in 75 ml of dimethylformamide at 40° to 50° C, whilst stirring. Thereafter the mixture is stirred for a further hour at 40° to 50° C. 10.3 g of 1-methyl-2-methylsulphonyl-5-nitro-imidazole dissolved in 75 ml of dimethylformamide are then added and the whole is stirred for a further hour at 90° to 100° C. Thereafter the reaction mixture is evaporated and the evaporation residue is triturated with 200 ml of water, filtered off and first washed thoroughly with water, then with isopropanol and finally also with petroleum ether. The crude product, which melts at 210°–213° C, is recrystallised from 50 ml of 2-ethoxyethanol. 1-[Pyridyl-(2)]-2-oxo-3-[1-methyl-5-nitroimidazolyl-(2)]-tetrahydroimidazole, thus obtained, of the formula

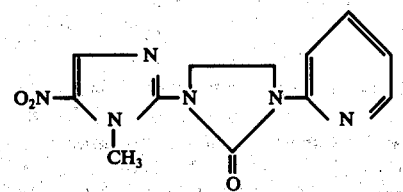

melts at 213°–215° C.

1-[Pyridyl-(2)]-2-oxo-tetrahydroimidazole used as the starting material, can be obtained, for example, by condensation of 2-aminopyridine with β-chloroethylisocyanate and subsequent cyclisation. It melts at 165°–166° C.

EXAMPLE 8

A solution of 8.1 g of 1-[1,3,4-thiadiazolyl-(2)]-2-oxo-tetrahydroimidazole in 150 ml of dimethylformamide is added dropwise over the course of 1 hour to a suspension of 2.3 g of 50% strength sodium hydride in 75 ml of dimethylformamide at 30° to 40° C, whilst stirring. Thereafter the mixture is stirred for a further hour at 30° to 40° C. 9.8 g of 1-methyl-2-methylsulphonyl-5-nitroimidazole dissolved in 75 ml of dimethylformamide are then added and the whole is stirred for a further hour at 90° to 100° C. Thereafter the reaction mixture is evaporated and the evaporation residue is triturated with 100 ml of water, filtered off and first thoroughly washed with water, then with isopropanol and finally also with petroleum ether. The crude product, which melts at 188°–190° C, is recrystallised from 85 ml of 2-ethoxyethanol. 1-[1,3,4-thiadiazolyl-(2)]-2-oxo-3-[1-methyl-5-nitro-imidazolyl-(2)]-tetrahydroimidazole, thus obtained, of the formula

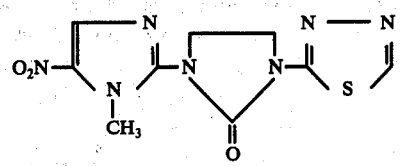

melts at 192°–194° C.

1-[1,3,4-Thiadiazolyl-(2)]-2-oxo-tetrahydroimidazole, required as the starting material, can be obtained, for example, by condensation of 2-amino-1,3,4-thiadiazole with β-chloroethylisocyanate and subsequent cyclisation. It melts at 240°–241° C.

EXAMPLE 9

A solution of 5.6 g of 1-[5-methylsulphonyl-thiazolyl-(2)]-2-oxo-tetrahydroimidazole in 75 ml of dimethylformamide is added dropwise over the course of 1 hour to a suspension of 1.1 g of 50% strength sodium hydride in 40 ml of dimethylformamide at 30°–40° C, whilst stirring. Thereafter the mixture is stirred for a further hour at 30°–40° C. 4.7 g of 1-methyl-2-methylsulphonyl-5-nitro-imidazole dissolved in 50 ml of dimethylformamide are then added and the whole is stirred for 1 hour at 90°–100° C. Thereafter the reaction mixture is evaporated and worked up as described in Example 8. The crude product, which melts at 222°–228° C, is recrystallised from 200 ml of 2-ethoxy-ethanol. 1-[5-Methylsulphonylthiazolyl-(2)]-2-oxo-3-[1-methyl-5-nitro-imidazolyl-(2)]-tetrahydroimidazole, thus obtained, of the formula

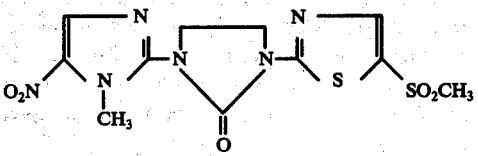

melts at 230° C–232° C, with decomposition.

1-[5-Methylsulphonyl-thiazolyl-(2)]-2-oxo-tetrahydroimidazole, required as the starting material, can be obtained, for example, by condensation of 2-amino-5-methylsulphonylthiazole with β-chloroethylisocyanate and subsequent cyclisation. It melts at 246° C.

EXAMPLE 10

A solution of 10.7 g of 1-[5-nitro-thiazolyl-(2)]-2-oxo-tetrahydroimidazole in 200 ml of dimethylformamide is added dropwise over the course of 1 hour to a suspension of 2.4 g of 50% strength sodium hydride in 75 ml of dimethylformamide at 20° C to 30° C, whilst stirring. Thereafter the mixture is stirred for a further hour at 20° C to 30° C. 10.3 g of 1-methyl-2-methylsulphonyl-5-nitro-imidazole, dissolved in 75 ml of dimethylformamide, are then added and the whole is stirred for a further hour at 80° C to 90° C. The reaction mixture is then acidified with glacial acetic acid whilst cooling with ice and is evaporated, and the evaporation residue is dissolved in 300 ml of ethylene chloride and extracted by shaking 5 times with 100 ml of water at a time. The ethylene chloride extract is dried with anhydrous magnesium sulphate and evaporated and the evaporation residue is first recrystallised from 60 ml of 2-ethoxyethanol and then again from 25 ml of 2-ethoxy-ethanol. 1-[5-Nitro-thiazolyl-(2)]-2-oxo-3-[1-methyl-5-nitro-imidazolyl-(2)]-tetrahydroimidazole, thus obtained, of the formula

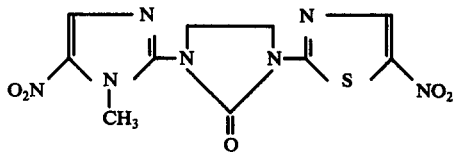

melts at 197°–199° C.

EXAMPLE 11

Tablets containing 250 mg of active substance are manufactured in the usual manner, for example to have the following composition per tablet:

| Composition | |
|---|---|
| 1-[Thiazolyl-(2)]-2-oxo-3-[1-methyl-5-nitro-imidazolyl-(2)]-tetrahydroimidazole | 250 mg |
| Lactose | 36 mg |
| Wheat starch | 100 mg |
| Colloidal silica | 16 mg |
| Talc | 16 mg |
| Magnesium stearate | 2 mg |
| | 420 mg |

MANUFACTURE

1-[Thiazolyl-(2)]-2-oxo-3-[1-methyl-5-nitro-imidazolyl-(2)]-tetrahydro-imidazole is mixed with the lactose, a part of the wheat starch and with colloidal silica and the mixture is forced through a sieve, whereby a powder mixture is obtained. A further part of the wheat starch is worked into a paste with a 5-fold amount of water on a water bath and the powder mixture is kneaded with this paste until a slightly plastic mass has been produced.

The plastic mass is forced through a sieve of approx. 3 mm mesh width and dried and the dry granules are again forced through a sieve. Thereafter the remaining wheat starch, talc and magnesium stearate are mixed in and the resulting mixture is pressed to give tablets weighing 420 mg (having a breaking groove).

I claim:

1. An imidazole compound of the formula

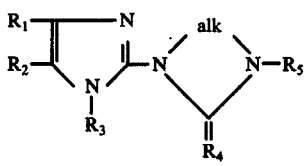

wherein one of the radicals $R_1$ and $R_2$ denotes hydrogen or lower alkyl and the other denotes a nitro group, $R_3$ is lower alkyl, hydroxy-lower alkyl, lower alkoxy-lower alkyl, $R_4$ is oxo, $R_5$ is thiadiazolyl-(2) and "alk" is ethylene, and the N-oxides and a therapeutically acceptable acid addition salt thereof.

2. An imidazole compound as claimed in claim 1 of the formula Ia

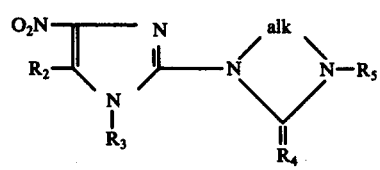

wherein $R_2$ is hydrogen or methyl, $R_3$ is 2-hydroxyethyl or methyl, $R_4$ is oxo, $R_5$ is thiadiazolyl-(2) and "alk" is ethylene and a therapeutically acceptable acid addition salt thereof.

3. An imidazole compound as claimed in claim 1 of the formula Ib

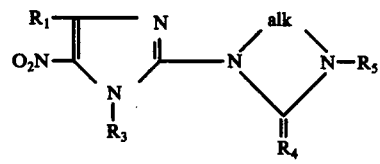

wherein $R_1$ is hydrogen or methyl, $R_3$ is 2-hydroxyethyl or methyl, $R_4$ is oxo, $R_4$ is thiadiazolyl-(2) and "alk" is ethylene and a therapeutically acceptable acid addition salt thereof.

4. A compound as claimed in claim 1 being 1-[1,3,4-thiadiazolyl-(2)]-2-oxo-3-[1-methyl-5-nitro-imidazolyl-(2)]-tetrahydroimidazole.

5. An antimicrobial pharmaceutical preparation comprising an antimicrobially effective amount of a compound as claimed in claim 1, together with a pharmaceutically usable excipient.

* * * * *